United States Patent [19]

Clement et al.

[11] 4,276,226
[45] Jun. 30, 1981

[54] METHYL- AND CHLORO- SUBSTITUTED AROMATIC DIKETODIOLS

[75] Inventors: Robert A. Clement; Burton C. Anderson, both of Wilmington, Del.

[73] Assignee: E. I. Du Pont de Nemours and Company, Wilmington, Del.

[21] Appl. No.: 59,890

[22] Filed: Jul. 23, 1979

[51] Int. Cl.³ .................. C09F 5/08; C07C 49/784; C07C 49/792; C07C 69/017
[52] U.S. Cl. .................. 260/410.5; 560/138; 560/139; 560/140; 560/141; 568/328; 568/333
[58] Field of Search .................. 260/410.5, 590 D; 560/138, 139, 140, 141

[56] References Cited

U.S. PATENT DOCUMENTS

| | | | |
|---|---|---|---|
| 3,530,091 | 9/1970 | Kitaoka et al. | 560/138 |
| 3,634,355 | 1/1972 | Barr et al. | 260/590 D |
| 3,729,447 | 4/1973 | Haberiand et al. | 260/590 D |
| 3,809,682 | 5/1974 | Studinka et al. | 260/590 D |
| 3,816,538 | 6/1974 | Haeck et al. | 260/590 D |
| 3,928,295 | 12/1975 | Rose | 260/591 |
| 3,979,459 | 9/1976 | Rose | 260/591 |

FOREIGN PATENT DOCUMENTS 591452 1/1978 U.S.S.R. .

Primary Examiner—Natalie Trousof
Assistant Examiner—Vera C. Clarke

[57] ABSTRACT

Aromatic diketones and diesters are provided of the formula

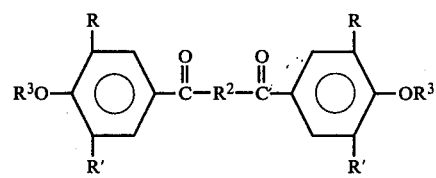

wherein R is independently methyl or chloro; R' is independently hydrogen or R; R² is 1,4-phenylene, 1,3-phenylene, 2,6-naphthylene, 4,4'-biphenylene, or 4,4'-biphenylene ether; and R³ is hydrogen or

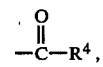

where R⁴ is a hydrocarbon group of 1–10 carbon atoms.

13 Claims, No Drawings

METHYL- AND CHLORO- SUBSTITUTED AROMATIC DIKETODIOLS

BACKGROUND OF THE INVENTION

1. Field of the Invention

This invention relates to certain substituted aromatic diketodiols and diesters thereof that are particularly useful for making melt-spinnable polyesters.

2. Description of the Prior Art

U.S. Pat. Nos. 3,928,295 and 3,979,459 disclose structural formulas of unsubstituted diketodiols.

U.S. Pat. Nos. 3,729,447 and 3,809,682 disclose structural formulas covering thousands of possible compounds including those of the present invention but not a single aromatic diketodiol is named or specifically described nor is a preparative method for compounds of the present invention provided.

SUMMARY OF THE INVENTION

The present invention is directed to diketodiols and diesters of the formula

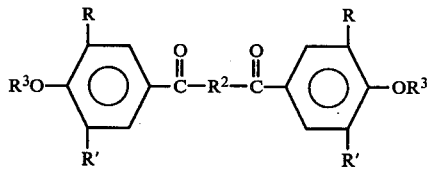

wherein R is independently methyl or chloro; R' is independently hydrogen or R; $R^2$ is 1,4-phenylene, 1,3-phenylene, 2,6-naphthylene, 4,4'-biphenylene, or 4,4'-biphenylene ether; and $R^3$ is hydrogen or

where $R^4$ is a hydrocarbon group of 1–10 carbon atoms.

These novel compounds may be reacted with aromatic dicarboxylic acids to form melt-spinnable polyesters.

DETAILED DESCRIPTION OF THE INVENTION

The diketodiols and diketodiesters of formula I wherein $R^2$ is 1,4-phenylene, 1,3-phenylene, 2,6-naphthylene and 4,4'-biphenylene, are prepared by reacting, under anhydrous conditions, a mono or disubstituted monophenol, such as o-cresol, 2,6-dimethylphenol or 2,6-dichlorophenol, with a diacid (or its diester) selected from the following: terephthalic acid, isophthalic acid, 2,6-naphthalene dicarboxylic acid and 4,4'-dicarboxybiphenyl in hydrogen fluoride in the presence of boron trifluoride. The reaction is allowed to proceed at about 0° to about 100° C., preferably 0° to 70° C.

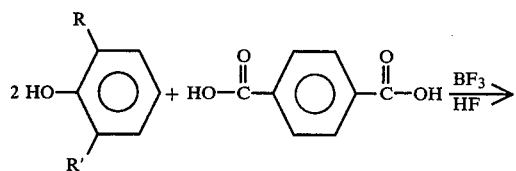

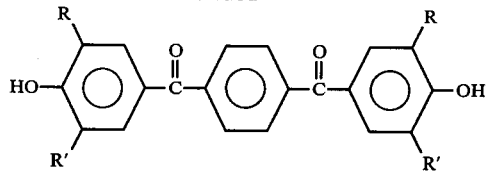

where R and R' are as defined above.

The diketodiols and diketodiesters of formula I wherein $R^2$ is

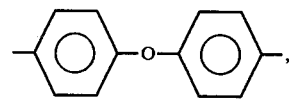

are prepared by reacting, in the manner indicated above, a mono or disubstituted 4-hydroxybenzoic acid, such as 3-methyl-4-hydroxybenzoic acid, 3,5-dimethyl-4-hydroxybenzoic acid, or 3,5-dichloro-4-hydroxybenzoic acid with biphenyl ether.

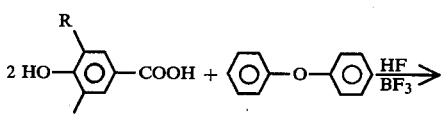

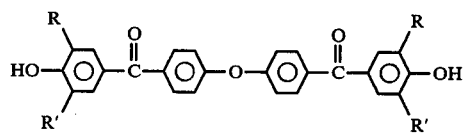

where R and R' are as defined above.

The diketodiols may be converted to esters by reacting with the appropriate carboxylic acid, e.g., acetic, propionic or benzoic acids, or, preferably, its anhydride (e.g. acetic anhydride) using a strong protic acid, such as sulfuric acid or trifluoromethanesulfonic acid, as catalyst.

Conversion of the diketodiols to esters, preferably acetates, as just described, facilitates purification, of importance for polymer preparation. Reaction by-products are partially removed during ester preparation, and remaining impurities are more readily removed from the ester, by washing and recrystallization, than from the diol.

The diketodiols of the invention may be reacted with one or more aromatic dicarboxylic acids to produce thermally stable polyesters.

The presence of substituents in the ortho positions of the terminal arylene groups in the diketodiols and diesters of formula I confers on polyesters prepared therefrom increased hydrolytic and in-rubber (amine-rich) stability as compared with similar polyesters wherein the ortho positions are unsubstituted. The ortho substituents may also modify polyester crystallinity and lower polymer melting point, thereby beneficially reducing polymer processing temperatures.

Methyl and chloro substituents ortho to the hydroxyl or ester groups in formula I compounds hinder the attack of other reactive species, such as diacids, on these groups. Thus the diketodiols and diesters of this invention undergo condensation polymerization with diacids at generally lower rates than aromatic diols or diesters which are unsubstituted in the ortho positions. Reduced polymerization rates offer positive advantages, especially in the preparation of copolyesters, by permitting the insertion of other, desired, monomer species into the growing polymer chains.

The polyesters may be prepared by melt polymerization techniques, at elevated temperatures, preferably under anhydrous conditions in an inert atmosphere, e.g. nitrogen or in vacuum. The reactants may be combined in a reaction vessel equipped with a stirrer, nitrogen inlet tube and combined distillation head-condenser (to facilitate by-product removal). The reaction vessel and other equipment are dried and purged with $N_2$ prior to use. The vessel and stirred contents, maintained under $N_2$, are heated, during which time the reactants polymerize and by-product (e.g. water, alcohols, phenols, or carboxylic acid) is removed and collected. Towards the end of the polymerization, the molten polymer may be placed under reduced pressure and heated further to complete the by-product removal and the polymerization. Optionally, the molten polymer may be transferred directly to an appropriate apparatus for preparation of shaped articles, e.g. a fiber spinning unit.

For smaller scale syntheses, e.g. in a polymer melt tube, agitation may be accomplished by passing a stream of inert gas through the melt.

The polyesters can also be formed into films, bars and other shaped articles by known techniques.

MEASUREMENTS AND TESTS

Melting points of the diketodiols and diesters thereof were determined by either of two methods. Where differential scanning calorimetry was noted as being employed, the procedure of ASTM D-3418-75 was followed. In all other instances, the oil bath capillary method of ASTM E-324-69 (Reapproved 1974) was used.

Polymer melt temperature (PMT) is that temperature at which a fresh polymer sample leaves a wet molten trail when stroked with moderate pressure across a clean metal surface. A temperature-gradient bar covering the range of 50°–400° C. was used for this determination (Beaman and Cramer, J. Polymer Sci., XII, pg. 227).

Inherent viscosity is defined by the following equation:

$$\eta inh = (\ln (\eta rel))/C$$

wherein ($\eta rel$) represents the relative viscosity and C represents a concentration of 0.5 gram of the polymer in 100 ml of solvent. The relative viscosity ($\eta rel$) is determined by dividing the flow time in a capillary viscometer of the dilute solution of the polymer by the flow time for the pure solvent. The dilute solutions used herein for determining ($\eta rel$) are of the concentration expressed by (C), above; flow times are determined at 30° C.; the solvent is a 40/60 mixture of 1,1,2,2-tetrachloroethane (TCE) and phenol.

The following examples are illustrative of the present invention.

EXAMPLE 1

1,4-Bis(3,5-dimethyl-4-hydroxybenzoyl)benzene

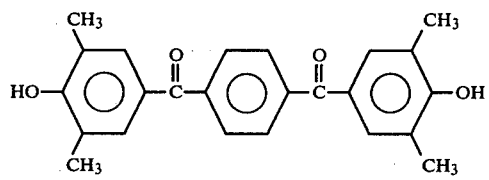

Terephthalic acid (33 g, 0.20 mole) and 2,6-dimethylphenol (48 g, 0.40 mole) were charged to a one-liter corrosion resistant nickel-base alloy (Hastalloy C®) shaker tube. The tube was cooled and anhydrous hydrogen fluoride (500 g) was distilled into the tube. The temperature of the tube was raised to 30° C. and it was pressured with gaseous boron trifluoride to a pressure of 50 psig. The tube was shaken for 4 hr at 30° C., cooled, and the bulk of the hydrogen fluoride was distilled from the tube at reduced pressure. The contents of the tube were then removed and consisted of crude product as a red solid.

The crude product was stirred with 2 l. of water, warmed, neutralized with sodium bicarbonate, and isolated by filtration of the warm mixture. This process was repeated, very little sodium bicarbonate being required, and the precipitate was rinsed with water, then with methanol, and air dried. There was obtained 64.5 g (86% yield) of product as a salmon-colored powder.

An analytical sample was obtained by two crystallizations of the product from dimethylsulfoxide/water, 500 ml/50 ml, in 61% recovery as a cream-colored powder. It had a m.p. (differential scanning calorimetry) of 333° C., and its elemental analysis was consistent with the formula $C_{24}H_{22}O_4$.

EXAMPLE 2

1,4-Bis(4-acetoxy-3,5-dimethylbenzoyl)benzene

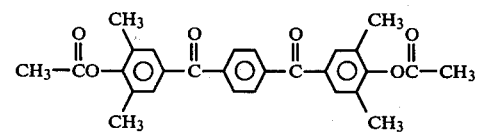

1,4-Bis(3,5-dimethyl-4-hydroxybenzoyl)benzene (148 g, 0.40 mole) was placed in a two-liter round-bottom flask which was equipped with a mechanical stirrer, a thermometer, and a water condenser through which the apparatus was attached to a source of nitrogen gas and vented to the atmosphere through a bubble tube. The reaction was run under an atmosphere of nitrogen. Acetic anhydride (163 g, 1.60 mole), acetic acid (550 ml) and trifluoromethanesulfonic acid (6.3 g) were added, and the mixture was stirred at ambient temperature for 94 hr. It was then stirred into 2 l. of water, filtered, and the precipitate was washed with water and air dried to afford a crude product in a yield of 174.7 g, as a light tan powder.

The product was stirred with 3500 ml of acetic acid, heated to boiling, cooled, and filtered. The precipitate was crystallized from acetic acid at a charge of 40 g/1250 ml, and afforded 1,4-bis(4-acetoxy-3,5-dimethylbenzoyl)benzene, analytically pure, as glistening yellow crystals, in a yield of 149.9 g (82%). It had a m.p. of 255°–256° C., and its elemental analysis was consistent with the formula $C_{28}H_{26}O_6$.

EXAMPLE 3

1,3-Bis(3,5-dimethyl-4-hydroxybenzoyl)benzene

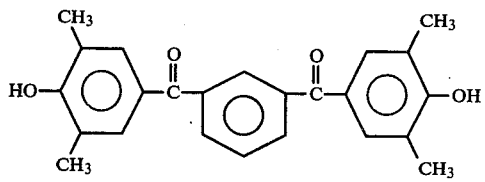

Isophthalic acid (66 g, 0.40 mole) and 2,6-dimethylphenol (96 g, 0.80 mole) were charged to a one-liter Hastalloy C ® shaker tube. The tube was cooled and hydrogen fluoride (400 g) was condensed in. The tube was then warmed to room temperature and pressured to 50 psig with boron trifluoride. The tube was then warmed to 50° C. and shaken 4 hr at 50° C. After being cooled and vented, the tube was discharged of its contents which was a dark red solution. This solution was allowed to evaporate in the hood. The dark red solid which resulted was stirred in 2 l. of water, heated to boiling, and the solid was isolated by filtration of the hot slurry. The precipitate was stirred in 2 l. of water, heated to boiling, and neutralized with sodium bicarbonate. Filtration of the hot slurry and air drying of the precipitate afforded the title product as a salmon-colored powder with an i.r. spectrum identical with that of the analytical sample. The yield was 136.5 g (91%).

The analytical sample was obtained by crystallization of 40 g of the above material from 450 ml dimethylsulfoxide/80 ml water, then from 175 ml dimethylsulfoxide/300 ml ethanol, and finally from 80 ml dimethylsulfoxide/100 ml ethanol. After being washed with ethanol and dried in a stream of nitrogen, pure product was obtained as a white granular powder. It had a m.p. (differential scanning calorimetry) of 280° C., and its elemental analysis was consistent with the formula $C_{24}H_{22}O_4$.

The diacetate of this diol, 1,3-bis(4-acetoxy-3,5-dimethylbenzoyl)benzene was prepared in a manner generally similar to that described in Example 2. The product melted at 177°–178° C. and its elemental analysis was consistent with the formula $C_{28}H_{26}O_6$.

EXAMPLE 4

2,6-Bis(3,5-dimethyl-4-hydroxybenzoyl)naphthalene

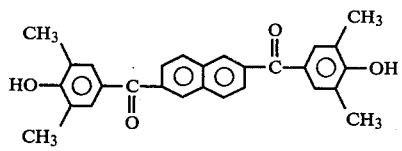

2,6-Naphthalenedicarboxylic acid (108 g, 0.50 mole) and 2,6-dimethylphenol (122 g, 1.00 mole) were charged to a one-liter Hastalloy C ® shaker tube. The tube was cooled and charged with hydrogen fluoride (400 g) and boron trifluoride (150 g). It was then heated to 50° C. and shaken for 4 hr at 50° C. The tube was cooled and vented, and the contents, a red solid in a red solution, was allowed to evaporate in the hood. The resulting red solid was stirred in 2 l. of water, warmed, and isolated by filtration of the warm solution. The precipitate was stirred with 2 l. of water, warmed, and neutralized with sodium bicarbonate. The warm mixture was filtered and the precipitate was washed with water, then methanol, and air dried. There was obtained 192.5 g (91%) of crude 2,6-bis(3,5-dimethyl-4-hydroxybenzoyl)naphthalene as an orange powder. 2,6-Bis(4-acetoxy-3,5-dimethylbenzoyl)naphthalene, the diacetate of the above diol was prepared in a manner generally similar to that of Example 2. It had a m.p. (differential scanning calorimetry) of 302° C., and its elemental analysis is consistent with the formula $C_{32}H_{28}O_6$.

EXAMPLE 5

4,4'-Bis(3,5-dimethyl-4-hydroxybenzoyl)biphenyl

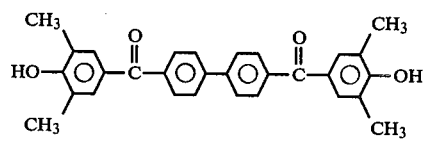

4,4'-Dicarbomethoxybiphenyl (67 g, 0.25 mole) and 2,6-dimethylphenol (61 g, 0.50 mole) were charged to a one-liter Hastalloy C ® shaker tube. The tube was cooled and charged with hydrogen fluoride (200 g) and boron trifluoride (75 g). The tube was heated to 50° C. and shaken at 50° C. for 4 hr. It was then cooled and vented, and the contents, an orange solid in an orange solution, were allowed to evaporate in the hood. The orange solid that resulted was stirred in 2 l. of water, warmed, and isolated by filtration of the warm mixture. The precipitate was stirred in 2 l. of water, warmed, and neutralized with sodium bicarbonate. The solid was isolated by filtration of the warm solution, washed with water, and air dried to afford crude 4,4'-bis(3,5-dimethyl-4-hydroxybenzoyl)biphenyl in a yield of 107.6 g (96%), as a salmon-colored powder.

4,4'-Bis(4-acetoxy-3,5-dimethylbenzoyl)biphenyl, the diacetate of the above diol was prepared in a manner similar to that of Example 2. It had a m.p. of 238°–239° C., and its elemental analysis was consistent with the formula $C_{34}H_{30}O_6$.

EXAMPLE 6

1,4-Bis(3,5-dichloro-4-hydroxybenzoyl)benzene

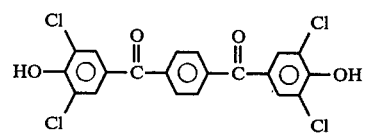

Terephthalic acid (41.5 g, 0.25 mole) and 2,6-dichlorophenol (81.5 g, 0.50 mole) were charged to a one-liter Hastalloy C ® shaker tube. The tube was cooled and charged with hydrogen fluoride (200 g) and boron trifluoride (75 g). The tube was heated to 90° C. and shaken for 4 hr at 90° C. The tube was cooled and vented and the contents, a mushy red solid, were allowed to evaporate in the hood. The red solid that resulted was stirred with 2 l. of water, warmed, and isolated by filtration of the warm slurry. It was again stirred with 2 l. of water, warmed, and neutralized with sodium bicarbonate. The solid was isolated by filtration, washed with water, and air dried. It amounted to 87.6 g (76%) of crude 1,4-bis(3,5-dichloro-4-hydroxybenzoyl)benzene as a dirty yellow powder. Its i.r. spectrum was consistent with its structure, exhibiting absorption attributable to conjugated ketone and phenolic hydroxyl groups.

1,4-Bis(4-acetoxy-3,5-dichlorobenzoyl)benzene, the diacetate of the above diol was prepared in a manner similar to that of Example 2. It had a m.p. of 245°–246° C., and its elemental analysis was consistent with the formula $C_{24}H_{14}O_6Cl_4$.

EXAMPLE 7

4,4'-Bis(3,5-dichloro-4-hydroxybenzoyl)biphenyl

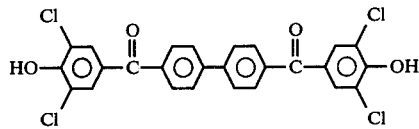

A one-liter Hastalloy C ® shaker tube was charged with 4,4'-dicarbomethoxybiphenyl (68 g, 0.25 mole) and 2,6-dichlorophenol (82 g, 0.50 mole). The tube was cooled and charged with hydrogen fluoride (400 g) and boron trifluoride (100 g). It was then heated to 70° C. and shaken at 70° C. for 8 hr. After being cooled and vented, the tube was discharged of its contents, a thick red paste, which was allowed to fume off in the hood. The residual orange solid was stirred in 2 l. of water, warmed, and recovered by filtration of the warm slurry. The solid was dispersed in water in a blender and recovered by filtration. It was then stirred in 2 l. of water, warmed and neutralized with sodium bicarbonate. The warm slurry was filtered and the precipitate was washed with methanol and air dried. It amounted to 112 g (84% yield) of crude product diol as an orange powder.

4,4'-Bis(4-acetoxy-3,5-dichlorobenzoyl)biphenyl, the diacetate of the above diol was prepared in a manner similar to that described in Example 2. It had a m.p. of 236°–237° C., and its elemental analysis was consistent with the formula $C_{30}H_{18}O_6Cl_4$.

EXAMPLE 8

4,4'-Bis(3,5-dimethyl-4-hydroxybenzoyl)diphenyl Ether

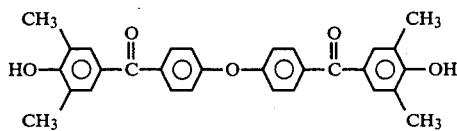

A one-liter Hastalloy C ® shaker tube was charged with 3,5-dimethyl-4-hydroxybenzoic acid (100 g, 0.60 mole) and diphenyl ether (51 g, 0.30 mole). The tube was cooled and charged with hydrogen fluoride (300 g) and boron trifluoride (136 g). It was then heated to 90° C. and shaken at 90° C. for 4 hr. After being cooled and vented, the tube was discharged of its contents, an orange-red solution, which was allowed to evaporate in the hood. The resulting red solid was stirred with 2 l. of water, warmed and filtered. The lumpy red precipitate was ground in a mortar. The resulting finely-ground solid was stirred with 2 l. of water, warmed and neutralized with sodium bicarbonate. Filtration of the warm slurry, afforded crude product diol, as a purple-pink powder which was washed with water and air dried. It amounted to 126 g (90% yield), and its i.r. spectrum was consistent with its structure, exhibiting absorption attributable to conjugated ketone and phenolic hydroxyl groups.

4,4'-Bis(4-acetoxy-3,5-dimethylbenzoyl)diphenyl ether, the diacetate of the above diol was prepared in a manner similar to that of Example 2. It had a m.p. of 172°–173° C., and its elemental analysis was consistent with the formula $C_{34}H_{30}O_7$.

EXAMPLE 9

4,4'-Bis(3,5-dichloro-4-hydroxybenzoyl)diphenyl Ether

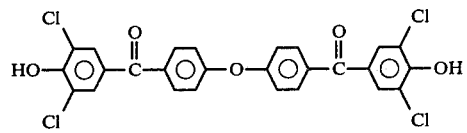

A one-liter Hastalloy C ® shaker tube was charged with 3,5-dichloro-4-hydroxybenzoic acid (104 g, 0.50 mole) and diphenyl ether (43 g, 0.25 mole). It was cooled and charged with hydrogen fluoride (400 g) and boron trifluoride (100 g), then heated to 30° C. and shaken at 30° C. for 4 hr. After being cooled and vented, the tube was discharged of its contents, an orange solution, which was allowed to evaporate in the hood. The resulting orange solid was stirred in 2 l. of water, warmed and recovered by filtration. It was dispersed in a blender with water and collected by filtration. The solid was then stirred with 2 l. of water, warmed, and neutralized with sodium bicarbonate. The solid was collected by filtration of the warm slurry, washed with water and dried to afford crude product diol as a salmon-colored powder in a yield of 123.7 g (90%). Its i.r. spectrum was consistent, showing absorption attributable to conjugated ketone and phenolic hydroxyl groups.

4,4'-Bis(4-acetoxy-3,5-dichlorobenzoyl)diphenyl ether, the diacetate of the above diol was prepared in a manner similar to that of Example 2. It had a m.p. of 182.5°–183° C., and its elemental analysis was consistent with the formula $C_{30}H_{18}O_7Cl_4$.

EXAMPLE 10

1,4-Bis(4-hydroxy-3-methylbenzoyl)benzene

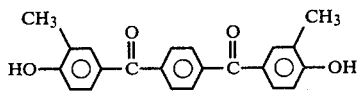

To a one-liter Hastalloy C ® shaker tube were charged terephthalic acid (83 g, 0.50 mole) and o-cresol (108 g, 1.00 mole). The tube was cooled, charged with hydrogen fluoride (400 g) and boron trifluoride (170 g), heated to 50° C., and shaken at 50° C. for 4 hr. The tube was cooled and vented and discharged of its contents, a pasty brown solid, which was allowed to fume off in the hood. The resulting solid was stirred in 2 l. of water, warmed and recovered by filtration of the warm slurry. It was then stirred in 2 l. of water, warmed, neutralized with sodium bicarbonate, and recovered by filtration of the warm slurry. After being washed with water and air dried, it amounted to 158.8 g (92% yield) of crude product diol as a tan-colored powder. Its i.r. spectrum was consistent, exhibiting absorption attributable to conjugated ketone and phenolic hydroxyl groups.

1,4-Bis(4-acetoxy-3-methylbenzoyl)benzene, the diacetate of the above diol was prepared in a similar manner to that described in Example 2. It had a m.p. of 211°–213° C., and its elemental analysis was consistent with the formula $C_{26}H_{22}O_6$.

EXAMPLE 11

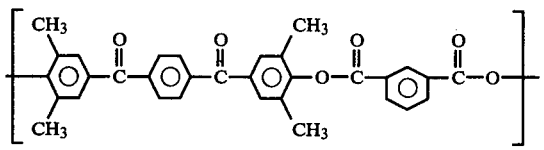

To a glass reactor with a nitrogen inlet and sidearm were added 2.29 g (0.005 mole) of 1,4-bis(4-acetoxy-3,5-dimethylbenzoyl)benzene and 0.83 g (0.005 mole) of isophthalic acid. The mixture was heated under a nitrogen atmosphere for 18 hr at 275° C. and for a further 6 hr at 283° C., followed by 3 hr at 283° C. under vacuum (<0.05 mm Hg pressure). A polyester of the above formula was obtained, having a polymer melt temperature of approximately 305° C. and an inherent viscosity of 0.53. X-ray crystallinity was low. Fibers were manually spun from the melt at about 185° C. to 250° C.

EXAMPLE 12

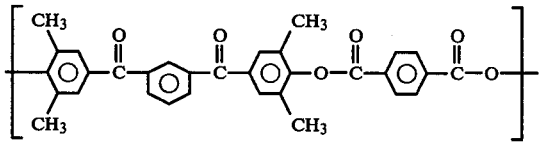

To a glass reactor with a nitrogen inlet and sidearm were added 2.29 g (0.005 mole) of 1,3-bis(4-acetoxy-3,5-dimethylbenzoyl)benzene and (0.005 mole) of terephthalic acid. The mixture was heated under a nitrogen atmosphere for 18 hr at 275° C. and for a further 6 hr at 283° C., followed by 3 hr at 283° C. under vacuum (<0.05 mm Hg pressure). The resulting polymer of the above formula had a polymer melt temperature (PMT) of 305° C., an inherent viscosity of 0.54, and could be manually spun into fibers at about 250° C. to 310° C. X-ray crystallinity was low.

Other polyesters prepared from diketodiols of the present invention are disclosed in the coassigned application Ser. No. 059,891, filed July 23, 1979 to A. H. Frazer filed on even date herewith.

We claim:

1. Diketodiol or diester of the formula

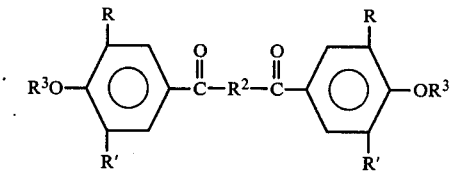

wherein R is independently methyl or chloro; R' is independently hydrogen or R; $R^2$ is 1,4-phenylene, 1,3-phenylene, 2,6-naphthylene, 4,4'-biphenylene or 4,4'-biphenylene ether and $R^3$ is hydrogen or

where $R^4$ is a hydrocarbon group of 1–10 carbon atoms.

2. A diketodiol or diester of claim 1 wherein $R^2$ is 1,4-phenylene.

3. A diketodiol or diester of claim 1 wherein $R^2$ is 1,3-phenylene.

4. A diketodiol or diester of claim 1 wherein $R^2$ is 2,6-naphthylene.

5. A diketodiol or diester of claim 1 wherein $R^2$ is 4,4'-biphenylene.

6. A diketodiol or diester of claim 1 wherein $R^2$ is 4,4'-biphenylene ether.

7. A diketodiol or diester of claim 1 wherein R and $R^1$ are the same and are methyl or chloro.

8. A diketodiol or diester of claim 7 wherein $R^2$ is 1,4-phenylene.

9. A diketodiol or diester of claim 7 wherein $R^2$ is 1,3-phenylene.

10. A diketodiol or diester of claim 7 wherein $R^2$ is 2,6-naphthylene.

11. A diketodiol or diester of claim 7 wherein $R^2$ is 4,4'-biphenylene.

12. A diketodiol or diester of claim 7 wherein $R^2$ is 4,4'-biphenylene ether.

13. A diketodiol or diester of claim 1 wherein R is methyl or chloro and $R^1$ is hydrogen.

* * * * *